United States Patent [19]
Klawitter et al.

[11] Patent Number: 5,782,927
[45] Date of Patent: Jul. 21, 1998

[54] METACARPAL-PHALANGEAL JOINT REPLACEMENT

[75] Inventors: Jerome J. Klawitter; William F. Ogilvie, both of Austin, Tex.

[73] Assignee: Ascension Orthopedics, Inc., Austin, Tex.

[21] Appl. No.: 743,717

[22] Filed: Nov. 6, 1996

[51] Int. Cl.$^6$ .................................................. A61F 2/42
[52] U.S. Cl. .................................... 623/21; 623/18
[58] Field of Search .......................... 623/18, 21, 22, 623/23

[56] References Cited

U.S. PATENT DOCUMENTS

| | | | |
|---|---|---|---|
| 3,946,445 | 3/1976 | Bentley et al. | 623/21 |
| 4,031,570 | 6/1977 | Frey | 623/22 |
| 4,231,121 | 11/1980 | Lewis . | |
| 4,242,759 | 1/1981 | White . | |
| 4,385,404 | 5/1983 | Sully et al. . | |
| 5,007,932 | 4/1991 | Bekki et al. | 623/21 |
| 5,405,399 | 4/1995 | Tornier | 623/21 |
| 5,405,400 | 4/1995 | Linscheid et al. | 623/21 |
| 5,405,401 | 4/1995 | Lippincott et al. | 623/21 |
| 5,413,609 | 5/1995 | Nicol et al. | 623/21 |
| 5,425,777 | 6/1995 | Sarkisian et al. | 623/21 |
| 5,443,516 | 8/1995 | Albrektsson et al. | 623/21 |

FOREIGN PATENT DOCUMENTS

| | | | |
|---|---|---|---|
| 611560 | 8/1994 | European Pat. Off. | 623/21 |
| 2605878 | 5/1988 | France | 623/21 |

OTHER PUBLICATIONS

Walker et al., "Laboratory Evaluation of a Metal-plastic Type of Metacarpophalangeal Joint Prosthesis", *Clinical Orthopedics and Related Research*, No. 112, pp. 349-356, Oct. 1975.

Linscheid et al., "Total Joint Arthroplasty", *Mayo Clinical Procedures*, vol. 54, pp. 516-526, Aug. 1979.

Unsworth et al., "Dimensions of the Metacarpo-phalangeal Joint with Particular Reference to Joint Prostheses", *Mechanical Engineering*, vol. 8, No. 2, pp. 75-80 (1979).

*Primary Examiner*—Mark O. Polutta
*Assistant Examiner*—Bruce E. Snow
*Attorney, Agent, or Firm*—Fitch, Even, Tabin & Flannery

[57] ABSTRACT

A joint prosthesis for replacement of the metacarpal-phalangeal (MP) joint of a human finger which includes a metacarpal element with a stem for reception into the medullary cavity of the metacarpal bone and a generally ball-shaped articular head and a phalangeal element with a stem for reception into the medullary cavity of the proximal phalangeal bone and a generally socket-shaped head which conforms to the ball-shaped head. The metacarpal element's articular head has reliefs located on each of its two lateral sides so as to provide a generally free path for the collateral ligaments. The phalangeal element's articular head has a dorsal protrusion, that resists subluxation-dislocation of the phalangeal bone, and grooves in its concave surface which allow biological fluids access to the inner regions of the articulation contact surfaces.

16 Claims, 4 Drawing Sheets

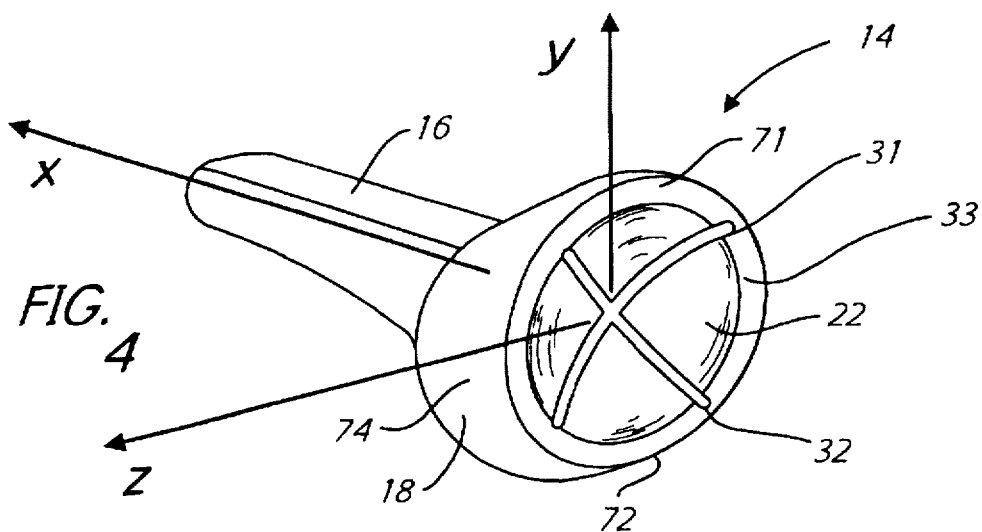
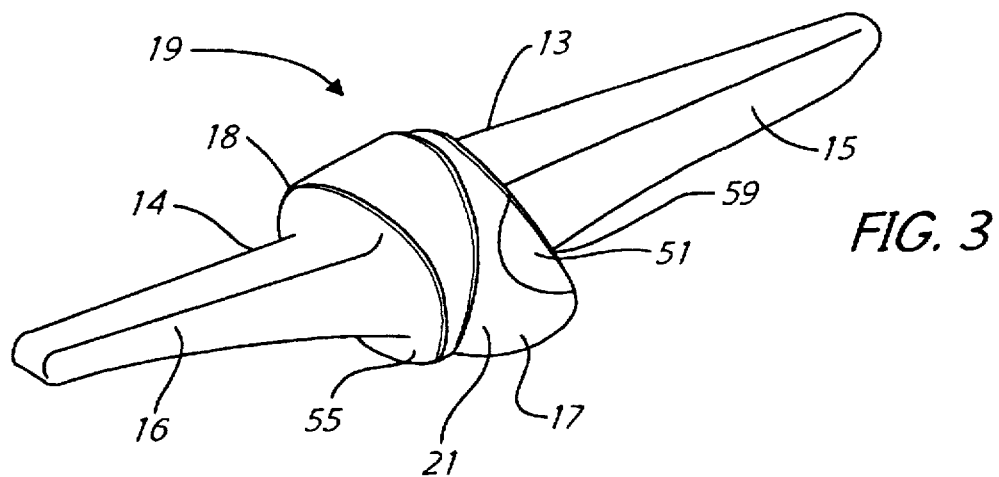
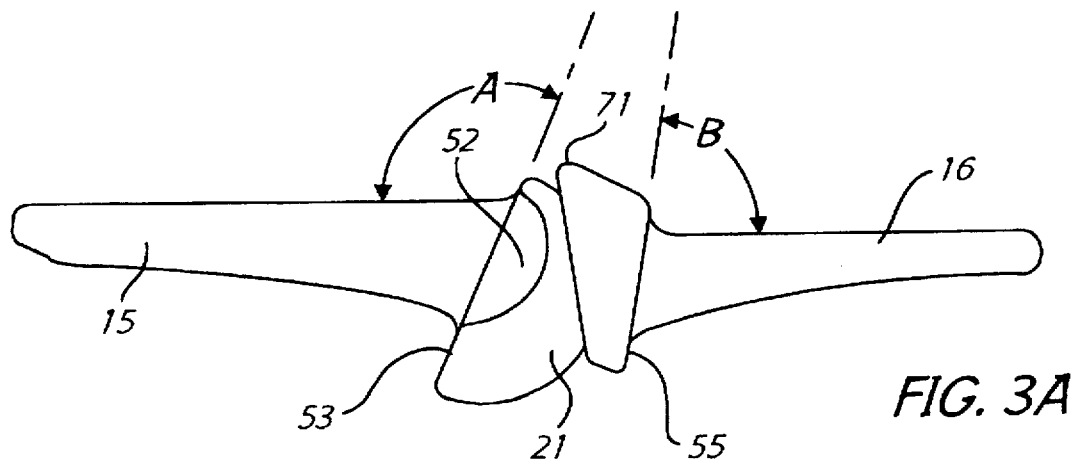

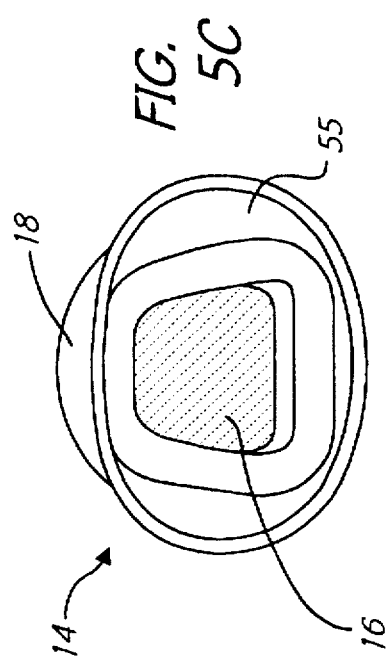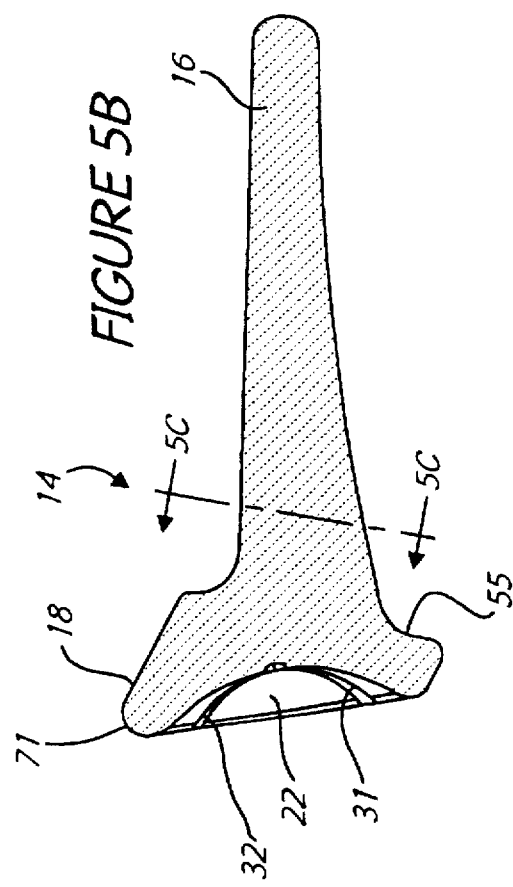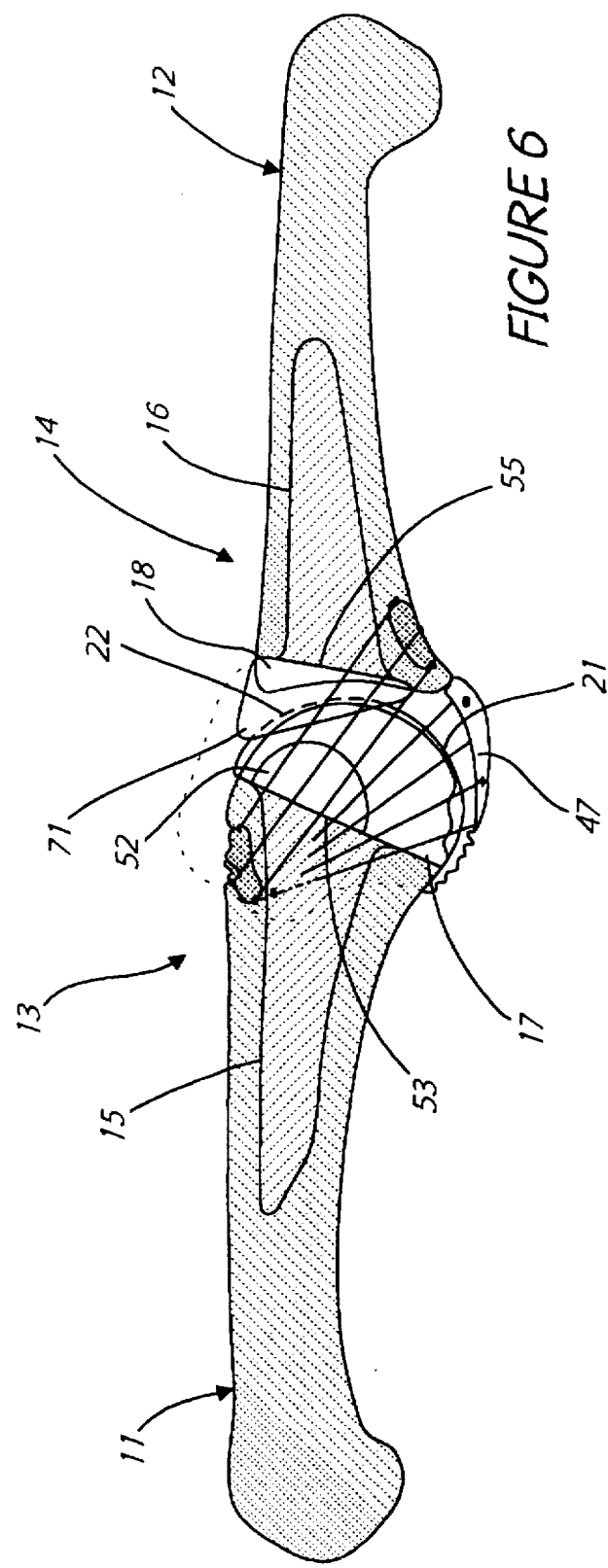

ical motion,
METACARPAL-PHALANGEAL JOINT REPLACEMENT

FIELD OF THE INVENTION

The present invention generally relates to prosthetic devices and more particularly to devices for replacement of the metacarpal-phalangeal (MP) joint of a human finger.

BACKGROUND OF THE INVENTION

The first elongated bone (metacarpal) at the base of each finger is connected to a proximal phalangeal bone through the metacarpal-phalangeal (MP) joint. This particular joint can be flexed or extended independently of the proximal or distal interphalangeal joint. This variable reciprocal motion, along with the opposability of the thumb, allows for the grasping of objects and the performance of daily functions which are of critical importance to humans. Damage to the MP joint through physical injury or disease can therefore be a severe physiological burden to inflicted humans.

Rheumatoid arthritis (RA), degenerative arthritis, and post-traumatic arthrosis of the MP joint cause interminable pain and poor function of the finger. Patients who have mild symptoms often respond to rest, immobilization, non-steroidal anti-inflammatory drugs, or intra-articular injections of steroids. However, patients who have more severe forms of arthritis may require total joint replacement of the MP joint.

The most common deformity in patients suffering from RA is induced by synovitis of the MP joint which often causes a narrowing of the articular cartilage of the MP joint and attenuation of the collateral ligament structure. The result is often palmar subluxation-dislocation of the proximal phalangeal bone which is caused by a laxity of the flexor complex on the palmar aspect of the MP joint. After loosening of this flexor complex, the action of the flexor tendons provides a dynamic force that palmarly subluxes-dislocates the proximal phalangeal bone. In addition, there is often a secondary loss of cartilage height by erosion and frequently a secondary change in bony architecture, producing a flattening of the metacarpal head and erosion of the dorsal lip of the proximal phalanx. The usual solution is installation of a MP prosthetic joint, see Linscheid et al., "Total Joint Arthroplasty", *Mayo Clin. Proc.*, 54:516-526 (1979); however, in such a case, there is a need for a replacement joint which resists subluxation-dislocation of the proximal phalangeal bone in the palmar direction.

A second important design consideration for MP prosthetic joints is minimizing the wear between the mating articulating surfaces. Mating surfaces may conform to such an extent that biological fluids which would normally provide joint lubrication are expressed from the MP prosthetic joint. The resulting "dry joint" may experience increased friction between the congruent articulating surfaces, as well as create an uncomfortable grinding and/or "squeaky" sensation to the recipient. Increased friction between the congruent articulating surfaces may result in increased wear of the MP prosthetic joint, thereby decreasing the service life of the prothesis. A MP prosthetic joint should preferably avoid exclusion of biological fluid from the congruent mating articulating surfaces.

Another important design consideration for MP prosthetic joints is providing a generally free path for the collateral ligaments which run along each lateral side of the MP joint and for the palmar ligaments or plate. The collateral ligaments of the MP joint comprise both fan-like collateral ligaments and cord-like collateral ligaments. The fan-like collateral ligaments insert at both sides of the distal portion of the first metacarpal bone and serve to support the palmar plate (sometimes called the volar plate) which attaches to the volar aspect of the proximal phalanx and forms a part of the MP overall joint. The cord-like collateral ligaments also insert in shallow depressions at both sides of the dorsal aspect of the distal portion of the first metacarpal bone and cross the MP joint to insert at the lateral volar sides of the proximally phalangeal bone. The cord-like ligaments are slack in extension of the MP joint, allowing for radial-ulnar motion, and are taut during flexion motion, prohibiting radial-ulnar motion. Proper MP prosthetic joint design should have concern for such ligaments.

Accordingly it is the object of the present invention to construct an improved MP joint prosthesis which allows essentially original and natural function to be restored to a damaged finger. To restore natural motion to a damaged finger, the MP prosthetic joint design should provide a free path for the collateral ligaments to run from the distally facing dorsal articular portion of the first metacarpal bone to the proximally facing palmar articular portion of the proximal phalangeal bone.

SUMMARY OF THE INVENTION

An implant device is provided to replace the MP joint of a human finger in the form of a prosthesis composed of two complementary elements or members. One member replaces the distal articular portion of the first metacarpal bone, and the other replaces the proximal articular portion of the proximal phalangeal bone. Preferably, the phalangeal member terminates in a socket which has a concave, generally spherical surface that receives, in articulating contact, a complementary, convex, generally spherical surface at the distal end of the metacarpal member. The articulating surfaces are substantially congruent, except for the preferred provision of a noncongruent groove means. Such groove means is preferably located in the phalangeal member's articular surface, and more preferably, it includes two generally perpendicular grooves, each orientated at about 45° to the plane of flexion-extension motion. Such grooves facilitate synovial lubricating fluid access to the articulating surfaces each time the MP joint member moves relative to each other.

The convex, generally spherical head of the metacarpal member has a relief means in the form of a pair of reliefs located laterally thereof. These reliefs provide generally free paths for the fan-like and cord-like collateral ligaments which generally run along each lateral side of the MP joint. The phalangeal member's proximal articular head combines an elliptical collar with a concave articulating surface of spherical curvature in a manner which results in a shape along its palmar aspect which does not disrupt the attachment sites of the collateral ligaments, avoids interference with the palmar ligament during flexion and provides a free path for the collateral ligaments. Also, the phalangeal member's concave, generally spherical surface has a rim-like dorsal protrusion that is located and shaped to extend over the articular surface of the head of the metacarpal member by a sufficient distance so as to resist volar subluxation-dislocation of the proximal phalangeal bone in the palmer direction.

The improved MP prosthetic joint realizes the aforementioned objects, features and advantages in a manner that is clearly evident from a thorough consideration of the detailed description when taken in conjunction with the drawings wherein there is shown and described illustrative embodiments of the invention.

3

BRIEF DESCRIPTION OF THE DRAWINGS

FIG. 3 is a side perspective view of an MP prosthetic joint embodying various features of the present invention showing the metacarpal element and phalangeal element in full extension, and particularly showing one relief which is cut laterally in the head of the metacarpal element.

FIG. 3A is a side elevation view of the MP joint of FIG. 3 looking from the opposite side.

FIG. 4 is a perspective view of a phalangeal element of FIG. 3.

FIG. 5B is a side section view taken along line 5B—5B of FIG. 5A.

FIG. 5C is a rear section view of the phalangeal element taken along line 5C—5C of FIG. 5B.

FIG. 6 is a side view, in partial section, of a first metacarpal bone and a proximal phalangeal bone in full extension with the replacement MP joint of FIG. 3 inserted therein.

DETAILED DESCRIPTION OF PREFERRED EMBODIMENTS

The present invention is directed to a joint prosthesis and to a method for the replacement of a diseased or damaged human joint. The preferred prosthesis is designed for permanent implantation in the human hand.

Because of the unique anatomy around the metacarpal-phalangeal joint, this joint can be flexed or extended independently of the proximal or distal interphalangeal joint. This variable reciprocal motion, along with the opposability of the thumb, is the hallmark of human dexterity.

Figure 1:
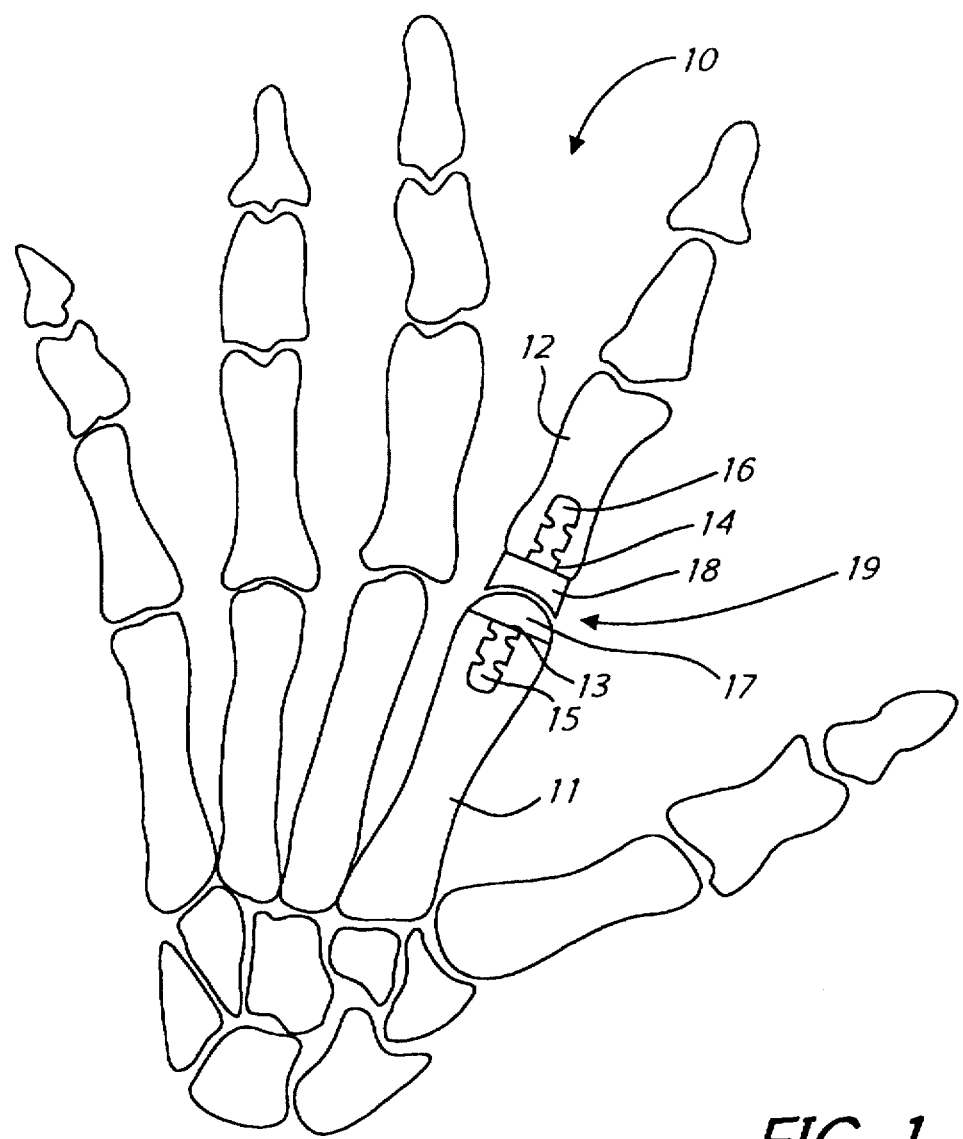
FIG. 1 is a schematic view, partially in section, of the human hand bone anatomy showing the general placement of an artificial MP joint.

In FIG. 1, a human right hand 10 is shown from the palmar perspective. The index finger contains a schematic representation of a MP prosthetic joint 19 located between the first metacarpal bone 11 and the proximal phalangeal bone 12. The MP prosthetic joint 19 comprises a first or metacarpal element 13, which is implanted in the first metacarpal bone 11, and a second or phalangeal element 14 implanted in the proximal phalangeal bone 12.

The metacarpal element 13 includes a stem portion 15, which is shaped to be received within the marrow or medullary cavity of the first metacarpal bone 11, and an articular head 17 which has a generally ball-shaped surface designed to replace the articular head of the first metacarpal bone 11. The phalangeal element 14 includes a stem portion 16, which is shaped to be received within the marrow or medullary cavity of the proximal phalangeal bone 12, and an articular head 18 which is generally socket-shaped and proportioned to conform to the metacarpal element's generally ball-shaped surface and replace the corresponding articular head of the proximal phalangeal bone 12. The stems 15 and 16 are schematically shown with optional grooves as are well known in this art.

4

Figure 5:
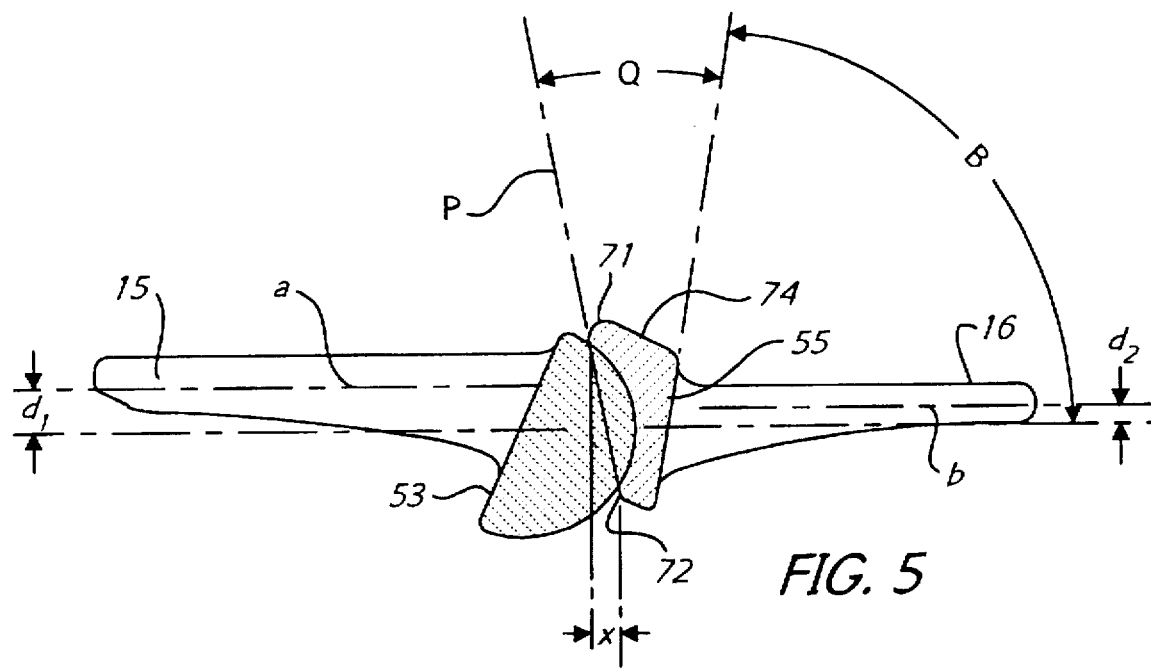
FIG. 5 is a side, partial sectional view of the MP replacement joint shown in FIG. 3A, illustrating various relevant angles of its construction.
Figure 5A:
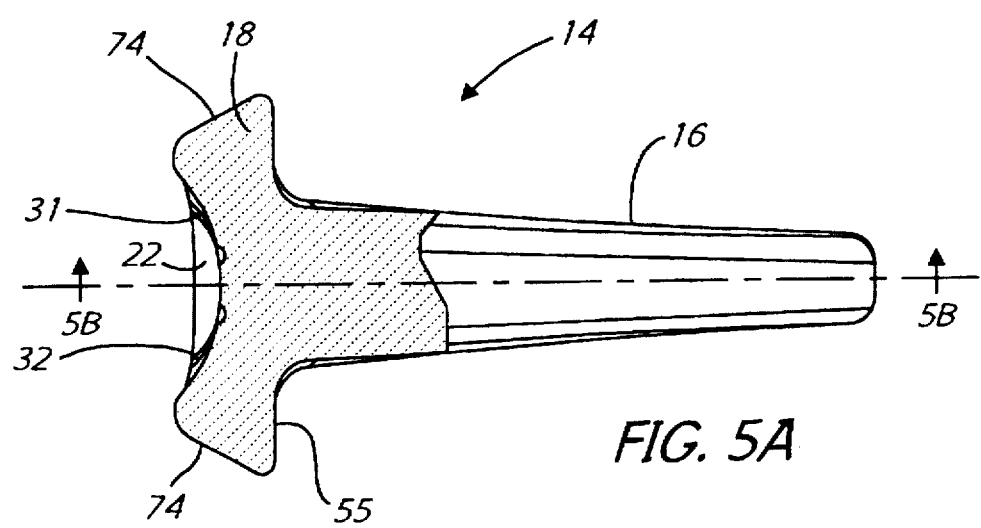
FIG. 5A is a top view of the phalangeal element with a portion broken away and shown in section.

Shown in FIG. 3 is a MP prosthetic joint 19 embodying various features of the invention wherein the metacarpal element 13 and the phalangeal element 14 are respectively formed at their ends with the heads 17 and 18 that provide articulating surfaces 21 and 22 of desired conforming shapes. The head of the phalangeal element 14 has a socket-shaped articulation surface 22 which is shaped to conform to a generally spherical or ball-shaped articulation surface of the metacarpal element 13, which is preferably substantially hemispherical. The head 17 is preferably a section of a sphere that extends about 5° to 10° of arc past the equator, and the illustrated head 17 has a major arc of about 190°, as best seen in FIGS. 3A and 5.

In the preferred embodiment, the articulation surface 22 of the phalangeal element 14 is a concave, surface of spherical curvature which is proportioned to conform with the metacarpal element's convex hemispherical surface 21, a section of which it receives in articulating contact. It is desirable that the surfaces 21 and 22 are such that their conforming articulating surfaces are substantially congruent. Preferably, the articulating surfaces 21 and 22 either have the same radius of curvature, or the metacarpal element's articulation convex surface 21 has a radius of curvature that is slightly smaller than the phalangeal element's radius of curvature. Such substantially congruent articulating surfaces should mate in such a way so as to closely emulate the ease of motion of the natural MP joint. As an exception, however, the articulating surface of the metacarpal element, or of the phalangeal element, or of both the metacarpal and phalangeal elements may preferably be formed with at least one non-congruent fluid-access groove within an articulating surface portion, as described in detail hereinafter.

The distal end of the first metacarpal bone 11 and the proximal end of the proximal phalangeal bone 12 are preferably cut during surgery at an angle off vertical, in order to preserve the collateral ligaments insertion in the palmar portion of the proximal phalangeal bone 12 and in the dorsal portion of the first metacarpal bone 11. More preferably, the surgical cuts are generally straight and positioned at the angles off vertical, as shown in FIG. 6. The surgical cut for the metacarpal bone should be made between about 20° and 30° to vertical and preferably at about 25° to vertical, i.e. at a dorsal angle of between about 110° and 120° to the centerline of the metacarpal bone. The phalangeal bone 12 should be cut at between about 5° and 150° to vertical and preferably at about 10° to vertical, i.e. of a dorsal angle of between 75° and 85° to the centerline of the phalangeal bone. Special tools are designed to surgically cut the bones accurately at the desired angles and to locate the position of the cuts on the long axes of the bone so as to maintain proper axial positioning of the metacarpal and phalangeal bones and preserve the sites of attachment of the ligaments.

FIGS. 3A, 5, 5A–5C and 6 show flat collars 53, 55 which surround the stems 15, 16 at the locations where they join the articular heads 17, 18. As shown in FIG. 6, the collars 53, 55 preferably seat squarely against the outer cortical shell portions of the surgically cut surfaces of the first metacarpal bone 11 and the proximal phalangeal bone 12, so as to provide firm support and avoid overloading the cancellous bone center portion. The collars 53, 55 are orientated at angles to coincide with the angle of the surgical cuts. As indicated in FIG. 3A, the surface of collar 53 is oriented at what is termed a dorsal angle A to the axis of the stem of the metacarpal element, which axis is parallel to the dorsal surface of the stem. This angle A is between about 110° and 120° and preferably about 115°, and the metacarpal bone is cut so as to coincide with the orientation of the collar 53. The flat surface of the collar 55 is oriented at a dorsal angle B of between about 75° and about 85° to the axis of the stem of the phalangeal element, which axis is also parallel to the dorsal surface of the stem, and preferably angle B is about 80°. The phalangeal bone 12 is cut to similarly coincide with this angle of orientation of the collar.

The stem portions 15, 16 may be slightly tapered to fit more easily into the long hollow medullary canals of the first metacarpal bone 11 and the proximal phalangeal bone 12, respectively, and they are formed with axes (marked "a" and "b" in FIG. 5) that will align with the respective axis of the medullary canal. As indicated above, the stem portions 15, 16 may optionally be provided with a plurality of undercuts and grooves, as schematically shown in FIG. 1, so as to promote stabilizing ingrowth of bone in these regions. The desired marrow cavities of the first metacarpal bone 11 and the proximal phalangeal bone 12 are preferably shaped during surgery, using a special broach, to achieve a snug fit with the stem portions. The stem portions 15, 16 can be secured within the marrow cavities using one of several methods, such as (1) bone growth into a porous coating or undulating surface of the stem portions 15, 16, (2) the use of bone cement, or (3) a tight mechanical fit of the stem portions 15, 16 within the marrow cavities. Preferably, the stem portions 15, 16 are bonded to the marrow cavities by means of a surface-active biological binding agent, such as hydroxyapatite.

The centerlines of a and b of such surgically created marrow cavities should correspond to the centerlines of the medullary canals of the first metacarpal bone and the proximal phalangeal bone, which are displaced slightly from the center of rotation of the MP joint. Preferably, the surgically shaped marrow cavities of the first metacarpal bone and the proximal phalangeal bone are each formed to accept the stem of a prosthetic element which has a centerline in the sagittal plane that is dorsal to the center of rotation of the articulation surface. The stem of the first metacarpal element has a centerline that is generally 2-3 mm dorsal to the center of rotation in the sagittal plane, as indicated by $d_1$ in FIG. 5. The phalangeal element has a centerline b that is offset about half as far as that of the metacarpal element, e.g. generally 0.8–1.7 mm dorsal to the center of rotation, as indicated by $d_2$ in FIG. 5. A particularly satisfactory anatomic alignment is achieved when the phalangeal element's stem 16 is offset from the metacarpal element's stem 15 in the palmar direction, preferably by approximately 1.5 mm in the palmar direction, for the average size human hand, i.e. $d_1 - d_2 = ~1.5$ mm. Because several sizes of metacarpal-phalangeal MP joints are preferably provided so that a surgeon will have a variety of sizes from which to choose, ranging from a small joint for a child to a joint for the hand of a large male, the centerline displacement is made proportional to the radius of the metacarpal head. The figures previously given are calculated for a ball-shaped metacarpal head having a radius of 6.5 mm. This ratio with the radius of the hemispherical metacarpal head so as to determine the centerline displacements in the MP joint of different sizes.

Figure 2:
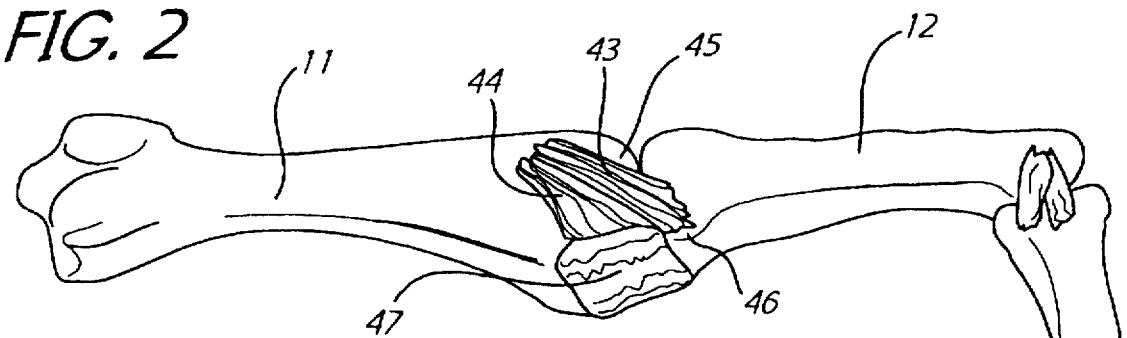
FIG. 2 is a side elevation view illustrating the arrangement of the collateral ligaments of the normal MP joint when the first metacarpal bone and proximal phalangeal bone are in full extension.

As best seen in FIGS. 3, 3A and 6, the generally hemispherical head 17 of the metacarpal element is provided with strategically located relief means in the form of a pair of reliefs 51, 52 located laterally thereof. Although a complementary relief may optionally be provided in the phalangeal element's head 18, this head is preferably shaped to avoid the need for specific reliefs. Each relief 51, 52 is shaped so as to provide a generally free path for the collateral ligaments past the edge of the head. As illustrated in FIG. 2, cord-like and fan-like collateral ligaments 43, 44 run generally along both lateral sides of the MP joint, from the dorsal aspect of the head of the metacarpal bone 11 to the palmar aspect of the proximal end of phalangeal bone 12. FIG. 6 schematically shows such collateral ligaments 43, 44 attached to the first metacarpal bone 11 on each lateral dorsal side in a finger in which the MP joint prothesis 19 has been inserted; joint prothesis is designed so that these ligaments cross the joint at approximately 45° and remain attached to the respective lateral palmar side of the proximal phalangeal bone 12. In particular, as seen in FIG. 2, fan-like collateral ligaments 44 normally run along each lateral side from a dorsal surface 45 of the first metacarpal bone to a volar plate 47 which incorporates a fibrous sheath that acts as a pulley to support the flexor tendon and is attached to a palmar surface region 46 at the proximal end of the proximal phalangeal bone. The cord-like collateral ligaments 43 run along each lateral side from the dorsal surface 45 of the first metacarpal bone to the palmar surface 46 of the proximal phalangeal bone.

In the preferred embodiment, the head of the metacarpal element is proportioned and shaped so as not to disrupt the attachment sites for the collateral ligaments and for the volar plate; its shape and positioning is preferably such that the sites of ligament attachment to the metacarpal head are retained. Generally, the otherwise hemispherical head 17 has reliefs 51, 52 located laterally thereof which are preferably formed by planar cuts but may alternatively have slightly concave surfaces, e.g. a shallow cylindrical surface. As an illustration, FIG. 3 shows the preferred planar relief 51 which is a flat surface that is formed by passing a plane to the long axis of the metacarpal element's stem 15, through the otherwise hemispherical head 17. Preferably, such pair of planar cuts are positioned to intersect the collar 53 and leave an arc of spherical surface at the collar of between about 30° to 90° on the dorsal side of the equator of the articular head 17 and an arc of approximately 120°–170° of spherical surface on the palmar side of the articular head 17.

The reliefs 51 and 52 may be alternatively formed in a variety of other manners. The reliefs 51 and 52 may be formed by planar cuts that are not parallel to the long axis of the metacarpal element's stem 15 or by a non-planar cut that generally corresponds to a shallow section of the surface of a circular or elliptical cylinder, e.g. an elliptical cylinder having an angle of approximately 15°.

The dimension of the edge 59 of each relief 51, 52, i.e. the length of such segments cut from otherwise circular collar, should be sufficient to provide a generally free path for the collateral ligaments 43, 44. Such edges 59, in order to provide the desired dorsal and palmar arc lengths, should be equal to between about 85% and 160% of the radius of the metacarpal element's hemispherical surface, and preferably between about 90% and 110%. The phalangeal element's articular head may also optionally have a relief located in each of its lateral sides, and in such an instance, when the first metacarpal bone 11 and the proximal phalangeal bone 12 are in full extension, such reliefs should complement the reliefs 51, 52 and be located to run generally continuously from the dorsal surface of the metacarpal element's articular head 17 to the palmer surface of the phalangeal element's articular head 18.

As best seen in FIG. 4, the outer circumference of the phalangeal element's articulation surface 22 terminates in a generally circular rim 33; however, as seen in FIG. 5C, the collar 55 has a generally elliptical shape. As indicated in FIG. 5, the rim lies in a plane (marked P) oriented an angle of between about 95° and 110° to the centerline axis of the phalangeal element's stem 16 and preferably at about 100°. As a result of construction with such an angle, the dorsal portion of the socket extends outwardly in the proximal direction to form a rim-like dorsal protrusion 71, as seen in FIGS. 3A, 5, 5B and 6, which protrusion 71 includes a portion of the concave articulation surface 22, and the construction also provides clearance at the palmar location. The rim-like dorsal protrusion 71 has a length in the axial direction so that it captures a sufficient portion of the metacarpal element's articular head to resist volar subluxation-dislocation of the proximal phalangeal bone 12 in the palmar direction. Even when the metacarpal and phalangeal elements of the prosthetic joint are in maximum extension (FIG. 6), the rim-like dorsal protrusion 71 extends above a major portion of the dorsal surface of the metacarpal element's articular head 17 to establish such phalangeal dorsal prominence. To achieve effective prominence, it is preferred that there is an arc of dorsal contact of at least about 50° between the concave surface of the phalangeal head and the convex surface of the metacarpal head; this arc is shown in FIG. 5, lying above the horizontal plane containing the center of rotation of the articulating surfaces. The length of the rim-like dorsal protrusion 71 does not however adversely effect the MP joint's normal range of motion, which is approximately 90° of flexion, approximately 20° of hyperextension, and approximately plus or minus 20° of radial-ulnar movement, during which desired contact between the conforming surfaces is retained.

From FIG. 5, it can be seen that, with the MP joint in full extension, the phalangeal element is oriented so that a palmar rim portion 72 of the circular rim 33 is located distal to the rim-like dorsal protrusion 71. The rim-like dorsal protrusion 71 is located a distance "x" beyond the palmar rim section 72 in the proximal direction along the axis of the stem 16, which is preferably equal to at least about 25% of the radius of the spherical surface of the head 17. This distance is dependent upon the orientation of the plane P in which the rim 33 of the socket is located, which plane is preferably oriented at about 100° to the stem axis. Because of its relative distal location and because the periphery of the head 18 is formed with surfaces 74 of converging orientation, as described hereinafter, the palmar rim section 72 avoids interference with the ligaments, including the palmar ligament 47, during flexion motion.

The lateral peripheral surfaces 74 of the head 18 of the phalangeal element generally increase in length from the palmar rim section 72 to the dorsal protrusion 71 because the plane of the collar 55 is oriented at an angle of between about 20° and about 30° to the plane P of the circular rim, which angle is preferably about 25° and is designated as "Q" in FIG. 5. The relative orientation of these two surfaces of the phalangeal element 14 at this angle, together with the converging shape of the lateral and palmar peripheral surfaces 74 of the head 18 create an environment where there is no interference with the adjacent collateral ligaments 44 and 46. The peripheral surfaces 74 which surround the rim 33 are rectilinear (see FIGS. 5A and 5B), which is preferable to facilitate manufacture. The orientation of the converging lateral, lateral-palmar and palmar peripheral surfaces 74 is preferably at an angle of between about 65° and 75° to the plane of the collar 55, with these rectilinear surfaces slanting inward, i.e. converging generally toward the centerline of the stem 15 of the facing metacarpal element. This convergence provides the clearance to assure lack of interference with the ligaments mentioned above.

To increase the service life of the prosthesis 19, it is desired that the articulating surface of the metacarpal element, or that of the phalangeal element, or those of both the metacarpal and phalangeal elements, be provided with at least one groove so as to allow lubricating biological fluid access to the MP prosthetic joint. More preferably, a pair of grooves are located in either the convex articular surface of the metacarpal element or in the concave surface of the phalangeal element. Most preferably, two transverse grooves 31 and 32 are located in the concave articulating surface 22 of the phalangeal element.

The groove arrangement should have sufficient length, width, and depth so as to carry synovial biological fluids to the inner portions of the congruent articulation surfaces, without adversely affecting the service life, range of motion, or ease of motion of the MP prosthetic joint. FIG. 4 shows the preferred embodiment of grooves 31, 32 located in the concave surface 22 of the phalangeal element 14. The grooves 31, 32 generally intersect at the center of the phalangeal element's articulating surface 22, and they extend outward from the center at 90° intervals to the outer circular rim 33 where the concave surface 22 terminates. Each groove 31, 32 thus traces a major spherical arc of the concave articulation surface 22.

Both grooves 31, 32 are preferably orientated transverse to the normal plane of flexion-extension motion so that synovial fluids are wiped over the articulating surfaces each time one element of the prosthetic joint 19 moves relative to the other. The MP joint has three differentially constrained planes of motion which are generally described as flexion-extension, ulnar-radial, and a conjunct rotation about the longitudinal axis with both flexion-extension and ulnar-radial motions. In FIG. 4, the phalangeal element 14 is shown marked with a coordinate system in order to orient the MP prosthetic joint with respect to its flexion-extension and ulnar-radial planes of motion. The MP joint's flexion-extension plane of motion and lateral ulnar-radial plane of motion are represented by the x-y plane and x-z plane, respectively.

FIG. 4 illustrates the most preferred embodiment wherein two intersecting grooves 31, 32 are located in the phalangeal element's concave articulating surface 22, terminating at the generally circular rim 33. The intersecting grooves 31, 32 are oriented so as to be transverse to the flexion-extension x-y plane and the ulnar-radial x-z plane, and each generally traces a major arc of the concave articulation surface 22. It is preferred that the intersecting grooves 31, 32 are orientated generally perpendicular to each other, lying in perpendicular planes. More preferably, each of the perpendicular grooves 31, 32 is transversely orientated at about 45° to the flexion-extension x-y plane of motion and thus also to the ulnar-radial x-z plane of motion.

The MP prosthetic joint elements 13, 14 are preferably made of biocompatible materials having a modulus of elasticity in the range of that of natural living bone, e.g. a graphite substrate coated with pyrolytic carbon. More importantly, the elements 13, 14 are made of materials having a sufficient hardness such that they will not distend significantly under the normal load to which they will be expected to be subjected during use. Such pyrocarbon exterior surfaces exhibit good wear resistance so that they will retain their original surface contours following years of implantation. If additional strength is felt desirable, the elements 13 and 14 may be formed from pyrolytic carbon deposited upon carbon-carbon fiber composite material, which exhibits high tensile strength.

Although the invention has been described with respect to preferred embodiments, various changes and modifications as would be obvious to one having ordinary skill in the art may be made without departing from the scope of the invention which is defined solely by the appended claims. For example, although the rim 33 of the socket is described as being generally circular, its edge may be formed with appropriate radii of curvature in an axial direction that may vary slightly about the circumferences thereof. Also, although the generally circular rim 33 of the socket is formed with a generally toroidal edge surface, other non-circular rim 33 surface shapes can be formed by varying the amount of socket capture in the dorsal, volar, radial or ulnar directions.

Particular features of the invention are emphasized in the claims which follow.

We claim:

1. A prosthetic device designed for replacement of a MP joint of a human finger comprising
   a metacarpal element having a stem portion which is shaped to be received within a metacarpal bone cavity, and an articular head portion which has a generally ball-shaped articular surface to replace the proximal articular portion of a metacarpal bone,
   a phalangeal element having a stem portion which is shaped to be received within a phalangeal bone cavity, and an articular head portion which has a generally socket-shaped articular surface and conforms to said ball-shaped surface and which is designed to replace a corresponding articular portion of a phalangeal bone; and
   said conforming articulating surfaces of said metacarpal and phalangeal elements being substantially congruent, except for groove means located in one of said articular surfaces which extends generally across and to the edge of said congruent articular surface and is orientated transverse to the plane of flexion-extension motion of said MP joint, so that it permits synovial fluid access at said edge into and out of inner regions of contact between the conforming articulating surfaces of said metacarpal and phalangeal elements.

2. The prosthetic device according to claim 1, wherein said articular surface of said metacarpal element is a convex spherical surface, and said articular surface of said phalangeal element is a concave spherical surface.

3. The prosthetic device according to claim 1, wherein said groove means is formed in said articular surface of said phalangeal element and includes two generally perpendicular grooves orientated at about 45° to said flexion-extension plane of motion.

4. The prosthetic device according to claim 1, wherein said articular head of said phalangeal element has (a) a rim-like dorsal protrusion that provides capture of said articular head of said metacarpal element so as to resist volar subluxation dislocation of said phalangeal element and (b) a palmar rim section which is sufficiently distal to said rim-like dorsal protrusion to provide clearance relative to the collateral ligaments of the human finger and avoid interference with the palmar ligament during flexion.

5. The prosthetic device according to claim 1 wherein said metacarpal element's articular head is provided with lateral relief means such that a generally free path is provided to allow the collateral ligaments to run from a dorsal/proximal edge of said articular head to a palmar/distal edge of said phalangeal element's articular head without interference.

6. The prosthetic device according to claim 5 wherein a relief means comprises a flat surface which is formed on each lateral side of said metacarpal element's articular head which is of otherwise generally hemispherical shape.

7. A method of treating a deteriorated MP joint of a human finger, which method comprises implanting the device according to claim 1 by (a) removing an articular portion of the first metacarpal bone of said deteriorated joint in a manner so as not to disturb collateral ligament attachment sites thereof and replacing the removed portion with said metacarpal element, and (b) removing an articular portion of said phalangeal bone of said deteriorated joint in a manner so as not to disturb sites of attachment of collateral ligaments and the palmar ligament and replacing the removed phalangeal portion with said phalangeal element.

8. The prosthetic device according to claim 1 wherein said groove means is formed in said articular surface of said phalangeal element and includes two grooves which intersect each other, each of which grooves is oriented transverse to the plane of flexion-extension motion and each of which extends to the edge of said congruent articular surface.

9. A prosthetic device designed for replacement of a MP joint of a human finger comprising
   a metacarpal element having a stem portion which is shaped to be received within a metacarpal bone cavity, and an articular head portion, which head portion has a generally ball-shaped surface to replace the distal articular portion of a metacarpal bone and has a flat collar section at the end of said stem portion, said flat section being oriented at a dorsal angle between about 110° and about 120° to the axis of said stem portion thereof; and
   a phalangeal element having a stem portion, which is shaped to be received within a phalangeal bone cavity, and an articular head portion, which has a concave surface shaped to conform to said ball-shaped surface and is designed to replace a corresponding articular portion of a phalangeal bone, said articular head portion having (a) a dorsal protrusion that provides capture of said articular head of said metacarpal element sufficient to resist volar subluxation, (b) a palmar rim section which is sufficiently distal to said dorsal protrusion so as to avoid interference with the palmar ligament of the finger during flexion and (c) a flat collar section at the end of said stem portion which is oriented at a dorsal angle of between about 75° and about 85°; and
   said metacarpal element's articular head being provided with relief means in the form of a flat surface located on each lateral side thereof which interrupts said otherwise ball-shaped surface so that, at the location of said collar, said ball-shaped head has a spherical arc of about 30° to 90° on the dorsal side of the equator and a spherical arc of about 120° to 170° on the volar side, whereby a generally free path is provided to allow the collateral ligaments to run without interference from a dorsal/proximal edge of said metacarpal element's articular head to a palmar/distal edge of said phalangeal element's articular head.

10. The prosthetic device according to claim 9 wherein said flat surface of said relief means has a length at said flat collar equal to approximately 85–160% of said radius of said hemispherical surface.

11. The prosthetic device according to claim 9 wherein said stem portion of said metacarpal element is offset a preselected distance dorsal to the center of rotation in the sagittal plane and said stem portion of said phalangeal element is offset a distance dorsal to said center of rotation at least about one-half of said preselected distance.

12. The prosthetic device according to claim 9 wherein said concave articular surface of said phalangeal element contains two generally perpendicular grooves orientated at about 45° to said flexion-extension plane of motion.

13. A method of treating a deteriorated MP joint of a human finger, which method comprises implanting a prosthetic device according to claim 9 by (a) removing an articular portion of said metacarpal bone by severing said bone at a dorsal angle between about 110° and 120° to the centerline of said bone without disturbing attachment sites for collateral ligaments on said bone, (b) replacing the removed metacarpal portion with said metacarpal element by inserting said stem portion thereof in the medullary canal of said bone, (c) removing an articular portion of the proximal phalangeal bone by severing said bone at a dorsal angle between about 75° and 85° to the centerline of said phalangeal bone without disturbing attachment sites for collateral ligaments on said bone, and (d) replacing the removed phalangeal portion with said phalangeal element by inserting said stem portion thereof in the medullary canal of said bone.

14. A prosthetic device designed for replacement of a MP joint of a human finger comprising a metacarpal element having a head with a generally hemispherical articular surface and a stem which is shaped to be received within a metacarpal bone cavity, and a phalangeal element having an articular socket-shaped head having a concave surface which conforms to said hemispherical articular surface and a stem which is shaped to be received within a phalangeal bone cavity, said phalangeal element including a flat generally elliptical collar section which encircles said stem portion and a generally circular rim that surrounds said concave surface of said socket, said socket-shaped head being formed with peripheral lateral, lateral-palmar, and palmar surfaces which are rectilinear and which surfaces converge from the periphery of said generally elliptical collar toward the centerline of said stem of said metacarpal element, terminatig at said generally circular rim.

15. The prosthetic device according to claim 14 wherein said rim is formed as a toroidal surface section and wherein said rectilinear lateral, lateral-palmar, and palmar surfaces are generally tangent to said toroidal rim, said toroidal rim lying generally in a plane at a dorsal angle of between about 95° and about 110° to the longitudinal axis of said stem portion thereof.

16. The prosthetic device according to claim 14 wherein said metacarpal element head is formed with a flat collar section at the end of said stem portion that is oriented at an angle between about 110° and about 120° to the axis of said stem thereof and wherein laterally located relief means intersects said flat collar and said otherwise hemispherical head at two lateral locations so that, at the location of said collar, said head has a spherical arc of about 30° to 90° on the dorsal side between said intersections and a spherical arc of about 120° to 170° on the palmar side between said intersections, providing a generally free path which allows collateral ligaments of a human finger, wherein said device is installed, to extend without interference from a dorsal/proximal edge of said metacarpal element head to a palmar/distal edge of said phalangeal element head.

* * * * *

UNITED STATES PATENT AND TRADEMARK OFFICE
CERTIFICATE OF CORRECTION

PATENT NO. : 5,782,927
DATED : July 21, 1998
INVENTOR(S) : Klawitter, et al.

It is certified that error appears in the above-identified patent and that said Letters Patent is hereby corrected as shown below:

IN THE CLAIMS:
Column 9, lines 34 and 47, change "orientated" to --oriented--.
Column 11, line 1, change "orientated" to --oriented--.

Signed and Sealed this

Twenty-second Day of December, 1998

Attest:

BRUCE LEHMAN

Attesting Officer     Commissioner of Patents and Trademarks